(12) United States Patent
Whitmore

(10) Patent No.: US 10,077,554 B2
(45) Date of Patent: Sep. 18, 2018

(54) CORROSION PROTECTION OF CABLES IN A CONCRETE STRUCTURE

(71) Applicant: David Whitmore, Winnipeg (CA)

(72) Inventor: David Whitmore, Winnipeg (CA)

( * ) Notice: Subject to any disclaimer, the term of this patent is extended or adjusted under 35 U.S.C. 154(b) by 128 days.

(21) Appl. No.: 15/211,466

(22) Filed: Jul. 15, 2016

(65) Prior Publication Data

US 2017/0096817 A1 Apr. 6, 2017

Related U.S. Application Data

(62) Division of application No. 13/585,180, filed on Aug. 14, 2012.

(51) Int. Cl.
| | |
|---|---|
| *C04B 20/10* | (2006.01) |
| *E04C 5/01* | (2006.01) |
| *C23F 11/00* | (2006.01) |
| *B28B 23/02* | (2006.01) |
| *E04C 5/08* | (2006.01) |
| *G01N 19/10* | (2006.01) |
| *D07B 7/12* | (2006.01) |
| *C04B 111/26* | (2006.01) |

(52) U.S. Cl.
CPC .............. *E04C 5/015* (2013.01); *B28B 23/02* (2013.01); *C04B 20/1014* (2013.01); *C23F 11/00* (2013.01); *D07B 7/12* (2013.01); *E04C 5/08* (2013.01); *G01N 19/10* (2013.01); *C04B 2111/26* (2013.01); *D07B 2201/2077* (2013.01); *D07B 2205/2046* (2013.01); *D07B 2205/30* (2013.01); *D07B 2205/3017* (2013.01); *D07B 2501/2023* (2013.01)

(58) Field of Classification Search
CPC ..... E04C 5/08; C04B 41/457; C04B 2111/26; C04B 2111/70; C04B 2111/723
See application file for complete search history.

(56) References Cited

U.S. PATENT DOCUMENTS

| | | |
|---|---|---|
| 5,460,033 A | 10/1995 | Velde |
| 2003/0101898 A1 | 6/2003 | Standke et al. |

FOREIGN PATENT DOCUMENTS

| | | |
|---|---|---|
| EP | 1176125 | 1/2002 |
| JP | 2003-155582 | 5/2003 |
| JP | 2004-041867 | 2/2004 |
| JP | 2006-233559 | 9/2006 |

*Primary Examiner* — William P Bell

(74) *Attorney, Agent, or Firm* — Adrian D. Battison; Ade & Company Inc.; Kyle R. Satterthwaite

(57) ABSTRACT

Steel reinforcing cables in concrete are protected against corrosion by injecting a carrier fluid and corrosion inhibitors into interstitial spaces between the wires of the cable at a first location along the cable and causing the fluid to pass through the interstitial spaces between the wires of the cable to a second location along the cable. The cable comprises an array of wires confined together and intimately surrounded by a covering material which is engaged with a periphery of the cable so that there are insufficient interconnected spaces between the cable and the covering material to allow passage of fluid longitudinally along the cable outside the cable itself. The method can be used with pre-stressed concrete, with post-tensioned bonded cables and with extruded un-bonded mono-strand cables.

36 Claims, 4 Drawing Sheets ns a divisional application of application
CORROSION PROTECTION OF CABLES IN A CONCRETE STRUCTURE This application is a divisional application of application Ser. No. 13/585,180 filed Aug. 14, 2012.

The present invention relates generally to the field of pre-stressed or post-tensioned concrete structures, and more particularly, to a method for protection of steel cables susceptible to corrosion in such concrete structures.

BACKGROUND OF THE INVENTION

Pre-tensioning of concrete is a method for improving the load carrying capacity of concrete structures. It can be used to produce beams, floors or bridges with longer spans and less deflection using thinner sections than is practical with ordinary reinforced concrete. Tendons used for pre-tensioning are generally made of high tensile steel cables and are used to provide an initial compressive load which produces a compressive stress that balances some or all of the tensile stress that the concrete member would otherwise experience due to a bending load. Pre-tensioning can be accomplished in three ways: pre-stressed concrete, and bonded or un-bonded post-tensioned concrete.

Pre-stressed concrete is cast around already tensioned cables. This method produces a good bond between the cable and concrete, which both protects the cable from corrosion and allows for direct transfer of loads between the cable and the concrete. The cured concrete adheres and bonds to the cables and when the load on the cables is released, much of it is transferred to the concrete as compression by static friction. However, it requires stout formwork and anchoring points between which the cable is stretched and held prior to the placement of the concrete. The cables are usually in a straight line unless deviators are installed in which case the cable will typically have straight segments. Most pre-tensioned concrete elements are prefabricated in a factory and must be transported to the construction site, which limits their size. Examples of pre-stressed elements include balcony elements, lintels, floor panels, double tees, beams and foundation piles.

Bonded post-tensioned concrete is the descriptive term for a method of applying compression after pouring and curing the concrete. The concrete is typically cast around a duct, which may be of plastic, steel or aluminium. The ducts are often curved or draped to follow the profile where they will provide the greatest structural benefit. One or more cables are generally fished through the duct after the concrete is poured. Once the concrete has hardened, the cables are tensioned by hydraulic jacks that react against the concrete member itself. When the cables have been tensioned sufficiently, they are wedged or clamped in position to maintain tension in the cables and compression in the concrete after the jacks are removed. The duct is then filled with a grout to protect the cables from corrosion.

Un-bonded post-tensioned concrete differs from bonded post-tensioning by providing each individual cable permanent freedom of movement relative to the concrete. To achieve this, each individual cable is typically coated with grease and enclosed by a plastic sheathing. In some cases the cable is a loose fit inside the sheath with the intention that the grease fills the space between the cable and the sheath. This construction can be formed by inserting the cable from one end into a pre-formed tubular sheath with the space between them being sufficient to allow the insertion to occur. In other cases the sheath is formed by covering the cable and surrounding grease with a strip of the covering material which is bent around the cable and then sealed or welded along a longitudinal seam to surround the cable.

In both cases the intention is that the cable is coated with grease and is sealed to prevent moisture entry and to ensure that the steel cable is maintained in a moisture free environment. In practical operation voids are typically present in this type of construction.

In another manufacturing system which is more typically used today for un-bonded mono-strand tendons, the cable is covered by grease and a plastic sheath is extruded onto the exterior of the cable as a tight envelope. In this case there are typically no voids and no path around the cable for moisture or other material to migrate along the sheath.

It is also intended that the sheath be continuous, complete and moisture impermeable. In practice the sheath is often damaged by its introduction into the forms, by failure to seal the ends of the sheath, or by the tensioning of the cable so that moisture can enter. Thus in the theoretical world, no moisture can enter into or migrate along the sheath so that no corrosion can occur. In practice corrosion typically does occur even to the extent of causing catastrophic failures if not detected and remediated.

The transfer of tension to the concrete is achieved by the steel cable acting against steel anchors embedded at the end of each cable. The main disadvantage over bonded post-tensioning is the fact that a cable can de-stress itself and burst out of the slab if damaged (such as during repair on the slab). The advantages of this system over bonded post-tensioning are:

a) The ability to individually adjust cables based on poor field conditions (For example: shifting a group of four cables around an opening by placing two to either side), b) The procedure of post-stress grouting is eliminated, and c) it is possible to de-stress the cables before attempting repair work.

In U.S. Pat. No. 5,365,779 (Vander Velde) issued Nov. 24, 1994 there is disclosed a method and apparatus for the corrosion condition evaluation of un-bonded pre-stressing elements in post-tension concrete structures. The method involves locating a pre-stressing element in the structure and providing at least two openings in the structure at positions along the length of the element. One of the openings is an inlet port and the other is an outlet port, each of the ports permitting communication with the gaseous environment within a conduit surrounding the pre-stressing element. The gaseous environment is accessed through the outlet port by extracting a sample of gas therethrough. The sample is then measured to determine its humidity and thereby evaluate the corrosion condition of the pre-stressing element between the inlet port and the outlet port. A method and apparatus is also provided for the on-site corrosion protection of the un-bonded pre-stressing elements whereby the gaseous environments within the conduits are cyclically pressurized with a dry gas for extraction of moisture which may lead to corrosion.

However as set forth in the above patent, the use of this method is limited to un-bonded post tensioning systems where there is enough space between the cable and its surrounding sheath to form a conduit to allow the passage of gas for sampling and for later drying if necessary or selected. WO 87/06958 assigned to Precision Dependability and Quality Testing discloses a method of treating a reinforced structure of masonry or cementitious material, such as concrete, to inhibit corrosion of the reinforcement. The method comprises inserting within the said material a vapour phase corrosion inhibitor so that the inhibitor migrates through the porous structure of the said material, and more-particularly along the interface between the said material and the reinforcement, to protect the reinforcement.

Again in this method there must be a channel or path around the reinforcement within the material to allow the passage of the vapour phase inhibitor.

However in regard to the other pre-tensioning methods defined above there is no channel or path for the passage of the protective fluid so that the above methods are not possible with such constructions.

The disclosures of the above patents are incorporated herein by reference.

This method of the present invention relates to the pre-tensioning system where the cable is intimately surrounded by the concrete itself.

This method of the present invention relates to the un-bonded post-tensioning system where the cable is contained within an extruded plastic sleeve extruded onto the cable and extending along the concrete member and there is provided an un-bonded filler material, generally grease, between the cable and the sleeve arranged to allow sliding of the cable within the sleeve during tensioning;

This method of the present invention relates to the bonded post-tensioning system where the cable is contained within a tubular container extending along the concrete member and the cable is intimately surrounded by a filler material, generally a cementitious grout, inserted into the tubular container after tensioning of the cable within the tubular container so that the grout is bonded intimately to the wires of the cable. Often multiple cables are installed in a single tubular container and the grout filler material fills and bonds intimately to all of the cables within the duct.

These methods now constitute a significant proportion of the installed pre-tensioned reinforcing systems so that a majority of the pre-tensioned structures cannot be protected using the methods of the above patents.

SUMMARY OF THE INVENTION

It is one object of the present invention therefore to provide a method for use with a steel reinforcing cable embedded in a concrete member which can be used to detect and/or treat corrosion of the cable in the concrete member.

According to a first aspect of the invention there is provided a method for use with a steel reinforcing cable embedded in a concrete member;

wherein the cable comprises an array of wires extending along the concrete for providing reinforcement thereto;

wherein the cable is intimately surrounded by a covering material which is engaged with a periphery of the cable so that there are insufficient interconnected spaces between the cable and the covering material to allow passage of fluid along the cable between the cable and the covering material;

the method comprising inserting a fluid into interstitial spaces between the wires of the cable at a first location along the cable and causing the fluid to pass through the interstitial spaces between the wires of the cable to a second location along the cable.

The present Applicant has found totally surprisingly that even in a situation where there is no path around the cable as required by the above prior art methods, there is a sufficient path within the interstices of the wires of the cable itself, even when under the high loads necessary for tensioning the concrete, to allow effective quantities of a fluid to pass along the cable.

In most cases, the fluid is selected so that it provides properties suitable to reduce corrosion of the steel wires of the cable.

In this case the fluid can contain corrosion inhibiting material such as corrosion inhibiting materials selected from the group consisting of:

Amines
Amino alcohol;
Amino carboxylate;
Calcium sulfonate;
Organofunctional silane, siloxane or silicone
Grease amine
Oil amine
Amine salts with nitrous or chromic acids,
Amine salts with carbonic acid, carbamic acid, acetic acid, substituted benzoic acids and organic esters of nitrous acid, phthallic acid or carbonic acid,
Primary, secondary and tertiary aliphatic amines,
Cycloaliphatic and aromatic amines,
Polymethylene amines,
Calcium nitrite, sodium nitrite,
mixtures of nitrites, urea, hexamethylene tetramine and ethanolamines, or
Nitrobenzene and 1-Nitronaphthalene.

Preferably the corrosion inhibiting material is Calcium sulfonate or Organofunctional silane.

The fluid can contain also or as an alternative Vapor Phase Inhibitors which are provided as a solid or liquid and have the properties of evaporation to provide a material which condenses into required locations to act as a corrosion inhibitor.

The carrier fluid can be a liquid or can be a gas. Where a gas is used this can operate as a drying agent to drive off any moisture from the area within or around the cable. Where a liquid is used this is typically a non-water-based liquid so as to avoid adding additional water which may be detrimental to the corrosion process or to drive out moisture by impregnating the volume around the cable with the liquid itself. The liquid or other carrier fluid may be selected to react with any water which may be present. If a water-based liquid is used, sufficient inhibitor or the use of some type of drying or other corrosion mitigation technique is recommended to minimize the risk of accelerating the corrosion of cables which may be contaminated with salt or otherwise already corroding.

Thus the liquid can be arranged to expel moisture from the interstitial spaces between the wires of the cable. In some cases depending on the surrounding material at the cable, the liquid can be arranged to generate an impregnated zone which can be hydrophobic at or around the cable by diffusing or spreading outwardly from the cable into the surrounding covering material so as to generate a hydrophobic zone around the cable.

In some cases the fluid interacts with the covering material to change its properties within the impregnated region.

In some cases the fluid interacts with the covering material to reduce permeability of the impregnated region.

In some cases the fluid interacts with the covering material to increase the electrical resistivity of the impregnated region.

In some cases the fluid forms a protective film on exposed portions of the wires.

In some cases the liquid is an oil or silicone based material generally of low viscosity which acts to displace any moisture and to fill any interstices where moisture may return thus preventing further corrosion. In other cases, the liquid may be selected so that it is arranged to increase in viscosity so that it remains more effectively in the location to which it has reached during the insertion process or to set-up to form a solid after inserting into the cable.

For example the liquid may be selected from the group consisting of

Silane, siloxane, silicone;

Oil

Alcohol or other organic solvent

Polymer resin

In some cases the liquid may also be the corrosion inhibiting material such as organofunctional silane, calcium sulfonate or amino alcohol. The liquid may also be water as described above.

In another arrangement as set out above the fluid comprises a gas arranged to effect a drying action on the wires of the cable to expel moisture from the interstitial spaces between the wires. Continued application of dry gas to the interstitial spaces between the wires may also dry the surrounding covering material over time. The introduction of gas may be used in a testing procedure to drive moisture or moisture-laden air from the interstitial spaces between the wires, which gas is then collected at the second location for analysis of a moisture content thereof. In this way an initial testing procedure can be provided which detects the presence of moisture and then goes onto a remediation process if moisture is detected.

In accordance with a second aspect of the invention, there is provided a method for use with a steel reinforcing cable embedded in concrete;

wherein the cable comprises an array of wires extending along the concrete for providing reinforcement thereto;

wherein the wires of the cable are intimately surrounded by the concrete;

the method comprising inserting a fluid into interstitial spaces between the wires of the cable at a first location along the cable and causing the fluid to pass through the interstitial spaces between the wires of the cable to a second location along the cable. Thus in this case the method is used with pre-stressed cables where the cable is buried into the concrete as the concrete is set.

In accordance with a third aspect of the invention, there is provided a method for use with a steel reinforcing cable embedded in a concrete member;

wherein the cable comprises an array of wires extending along the concrete member for providing reinforcement thereto;

wherein the cable is contained within a tubular container extending along the concrete member;

wherein the wires of the cable are intimately surrounded by a filler material inserted into the tubular container after tensioning of the cable within the tubular container where the filler material is bonded intimately to the wires of the cable;

the method comprising inserting a fluid into interstitial spaces between the wires of the cable at a first location along the cable and causing the fluid to pass through the interstitial spaces between the wires of the cable to a second location along the cable.

Thus in this case the method is used with post tensioned bonded cables where the cable is buried in a grout injected into the tubular sleeve after tensioning.

In accordance with a fourth aspect of the invention, there is provided a method for use with a steel reinforcing cable;

wherein the cable comprises an array of wires confined together to form an elongate cable;

wherein the cable is contained within an extruded plastic sleeve extruded onto the cable so as to enter into external interstices between the wires around the cable;

the cable and the plastic sleeve extending along the concrete member;

wherein there is provided an un-bonded filler material in the external interstices between the cable and the sleeve arranged to allow sliding of the cable within the sleeve during tensioning;

the method comprising inserting a fluid into interstitial spaces between the wires of the cable at a first location along the cable and causing the fluid to pass through the interstitial spaces between the wires of the cable to a second location along the cable.

Thus in this case the method is used with post tensioned un-bonded cables where the cable is contained within an extruded plastic sleeve.

In accordance with a further aspect of the invention, there is provided a method for use with a steel reinforcing cable embedded in a concrete or mortar or grout covering material;

wherein the cable comprises an array of wires confined together to form an elongate cable extending along the concrete for providing reinforcement thereto;

the method comprising introducing a liquid into the interstitial spaces within the cable at a first location along the cable and causing the fluid to pass along the cable to a second location along the cable;

and causing the liquid arranged to spread outwardly from the cable to impregnate into the surrounding covering material so as to generate an impregnated zone around the cable.

This impregnated zone may be hydrophobic, it may be impregnated with corrosion inhibiting material, or it may be impregnated to provide high electrical resistance. The impregnation of the covering material may otherwise modify the properties of the covering material such as providing reduced porosity, reduced permeability, waterproofing or increased strength.

Thus in this aspect, the injection of the liquid such as oil, amino alcohol, calcium sulfonate or silane has been found to cause the liquid to diffuse or migrate outwardly into a surrounding volume of concrete or mortar surrounding the cable to form a generally cylindrical impregnated zone around the cable. In the case of injection of silane based material, the reaction of the silane with the concrete has created a hydrophobic layer of concrete surrounding the cable into which it is difficult for moisture to penetrate.

The injection of the fluid into the cable can occur at ends of the cable where the wires of the cable are exposed so that the injection occurs directly into the interstices between the wires. In this case the second location may be at the other end or may be at an intermediate location. Alternatively, surprisingly, injection of the fluid into the cable can occur at an intermediate location of the cable is also possible where the injection is at the periphery of the cable requiring the fluid to penetrate from the periphery into the interstices between the wires. Both techniques have been shown to operate satisfactorily.

The injection typically will require some pressure but this has been found that a relatively low pressure of the order of 50 to 100 psi for low viscosity liquids are suitable to travel the length of the cable, coat the exposed steel surfaces, impregnate the concrete surrounding the cable, drive off moisture and carry the corrosion inhibitor. Higher pressures may be required for longer lengths, higher viscosity liquids or semi-liquid materials such as grease. Vacuum can be used at the downstream end either in addition to or as a replacement to the pressurized supply. Gas can be injected in the same manner either as air for drying or as a vapor for vapor deposition of Vapor Phase Corrosion inhibitors.

The ends or intermediate locations may be already exposed or may be located by drilling to the cable or by other excavation methods. Intermediate locations may be excavated to expose one face of the cable or the excavation may extend around the periphery of the cable.

Various inhibitors may be used in the method of the invention, provided they are chemically suited to inhibiting corrosion of whatever reinforcement is used. The inhibitor for ferrous metal reinforcement may for example be, or include, at least one material selected from (i) Amine salts with nitrous or chromic acids, (ii) Amine functional groups attached to polymer chains including alcohols and silanes, (iii) Amine salts including those with carbonic acid, carbamic acid, acetic acid, substituted benzoic acids and (iv) organic esters of nitrous acid, phthallic acid or carbonic acid, (v) Primary, secondary and tertiary aliphatic amines, (vi) Cycloaliphatic and aromatic amines, (vii) Polymethylene amines, (viii) nitrite salts, mixtures of nitrites with urea, hexamethylene tetramine and ethanolamines, or (ix) Nitrobenzene and 1-Nitronaphthalene, (x) Calcium and other sulfonates, (xi) Organofunctional silanes and siloxanes.

The corrosion inhibitor can be in liquid form or may be a Vapor Phase Inhibitor (VPI). The preferred VPI's for protecting ferrous metal (usually steel) reinforcement by the method of the present invention are dicyclohexylamine nitrite (DCHN), cyclohexylamine benzoate (CHAB) and cyclohexylamine carbamate (CHC), more preferably a mixture of CHAB and CHC. These are both white solids and have the following structures: CHAB 0–$NH_3$+$O_2C$ CHC $NH_3$+O—C—NH-0 Mixtures of fast-acting and slow-acting VPI's have the advantage of combining fast initial action with extended service life. Thus the inhibitor preferably comprises at least two vapour phase inhibitor compounds, at least one of which vaporises relatively slowly and at least one other of which vaporises relatively quickly under the conditions to be encountered by the concrete structure in service.

DETAILED DESCRIPTION

Figure 1:
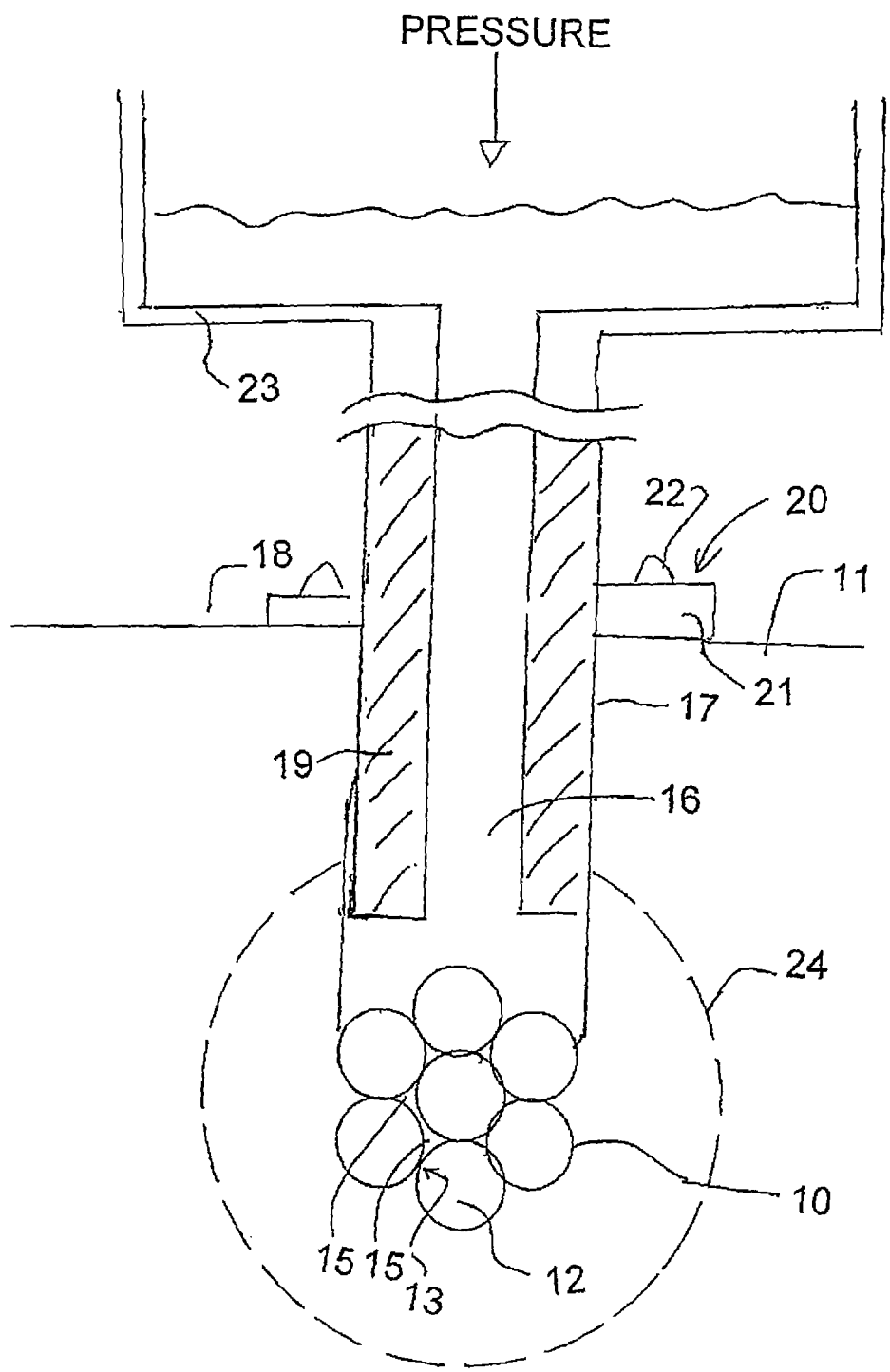
FIG. 1 is a vertical cross-sectional view transversely through a concrete member at an injection site for a fluid into the interstices of a reinforcing pre-stressed cable in a method according to the present invention.

In FIG. 1 is shown a pre-stressed steel reinforcing cable 10 embedded in a concrete member 11. The cable 10 comprises an array of wires 12 confined together and under tension. Typically the wires are wound around a helix at a shallow angle so as to hold them as a confined array with each wire butting against its neighbours and held in contact with its neighbours by the loads therebetween generated by the tension on the helical array. Thus each wire has its surface in direct contact with its neighbour along its length as indicated at 13.

In the pre-stressed system shown in FIG. 1, the cable is intimately surrounded by the concrete itself by casting of the concrete while the cable is in place in the form so that the concrete is engaged with a periphery of the cable at the peripheral surface of the outermost wires. Thus the concrete in the casting process butts intimately with all of the peripheral surfaces of the wires and prevents the formation of any spaces around the cable to allow passage of fluid longitudinally along the cable in spaces between the cable and the covering material. Thus there are in effect no interstitial spaces and certainly no interconnected interstitial spaces between the cable and the covering material itself.

However the wires themselves remain separate and leave interstitial spaces 15 between each wire and its neighbours. The method of the present invention therefore comprises inserting a fluid 16 into the interstitial spaces 15 between the wires of the cable.

The fluid is injected or inserted at a first location along the cable and the fluid is caused to pass through the interstitial spaces between the wires of the cable to a second location along the cable. The location in FIG. 1 is at a position along the length of the cable so that a hole 17 is drilled to intersect the cable from a surface 18 of the concrete member to the cable so that one side face of the cable is exposed in the hole. A tube 19 is inserted into the hole and held in place by an adhesive or by a suitable coupling 20 which holds the tube in place to resist the pressure in the fluid tending to displace the tube. Alternatively, the hole may be excavated and may extend around the periphery of the cable at the location of the excavation. Many different mounting arrangements can be used and one example only is shown where a flange 21 is fastened to the surface 18 by screws 22.

The fluid 16 is provided by a pressurized container 23 which is attached to the tube. The container can be of any arrangement depending on the pressure to be applied. In one example the pressure is of the order of 50 to 100 psi which requires only a plastic container with a hand pump for generating the pressure. In other cases a pressure pump, pressure pot, piston pump, gear pump, hydraulic cylinder or compressor may be used to generate the required fluid pressure to enable the material to flow. Depending on the type of pumping and associated measuring devices, the applied pressure and flow rate can be adjusted and monitored. Intermediate holes can be provided to monitor the movement of the fluid along the length of the cable or to progressively insert the fluid into the cable, section by section to minimize the distance the fluid is required to flow from each injection location. Vacuum may be applied at a position separate from the point of application of the fluid to assist in flow and penetration of the fluid along the length of the cable.

The fluid 16 at the side face of the cable can penetrate between the wires into the interstices 15 into the interstices of the wires within the cable itself. From those interstices the fluid can pass along the cable to a second location. The second location not shown in FIG. 1 can be at an end of the cable or can be at another intermediate location on the cable. In order to complete protection of a long length of cable, a number of locations along the cable can be selected and fluid injected to pass along the cable to a next location.

The fluid 16 is selected as defined above so that it includes a carrier as defined and a corrosion inhibitor as defined which provides properties suitable to reduce corrosion of the steel wires of the cable. The corrosion inhibitor may improve the durability of the structure by improving or modifying the properties of the surrounding concrete. The carrier and the corrosion inhibitor may in some cases be the same material. As the corrosion inhibitor has the above properties and is preferably one of the materials defined hereinafter, the corrosion inhibitor is necessarily different from the covering material which, as explained above is the concrete itself, a surrounding grout or grease.

In FIG. 1 the fluid includes a liquid carrier which may expel moisture or react with moisture from the interstitial spaces 15 between the wires of the cable and impregnate the surrounding concrete to generate a hydrophobic zone 24 around the cable by diffusing or spreading outwardly from the cable into the surrounding concrete. The fluid may also act to coat the wires and form a protective film on the surface of the wires. The interior wire surfaces may be largely or fully coated. The exterior wire surfaces in direct contact with the surrounding concrete and may receive only a partial protective film coating. The use of a fluid which acts to coat the wires and form a protective film is particularly beneficial to provide corrosion protection to steel wire surfaces which are exposed to air bubbles, voids or pockets in the surrounding concrete, grout or filler material at certain points along the length of the cable. The fluid can reach these bubbles, voids or pockets via the interstitial spaces even though they are not interconnected through the covering material.

Thus the injection of the carrier liquid such as oil, amine, amino alcohol, calcium sulfonate, silane, siloxane, silicone, organic solvent or other polymer causes the liquid to diffuse or migrate outwardly to impregnate into a surrounding volume of concrete or mortar surrounding the cable to form a generally cylindrical impregnated zone around the cable. Depending on the material used it may be difficult for moisture to penetrate. The fluid may be free of water. The fluid can be selected so that it interacts with the covering material to change the properties of the covering material within the impregnated region. Thus for example, the fluid interacts with the covering material to reduce permeability of the impregnated region. Thus for example, the fluid interacts with the covering material to increase the electrical resistivity of the impregnated region. Thus for example, the fluid forms a protective film on exposed portions of the wires. Thus for example, the impregnated zone around the cable includes a corrosion inhibiting material. Thus for example, the impregnated zone around the cable has an increased electrical resistance. Thus for example, the impregnated zone around the cable has a reduced permeability.

Figure 2:
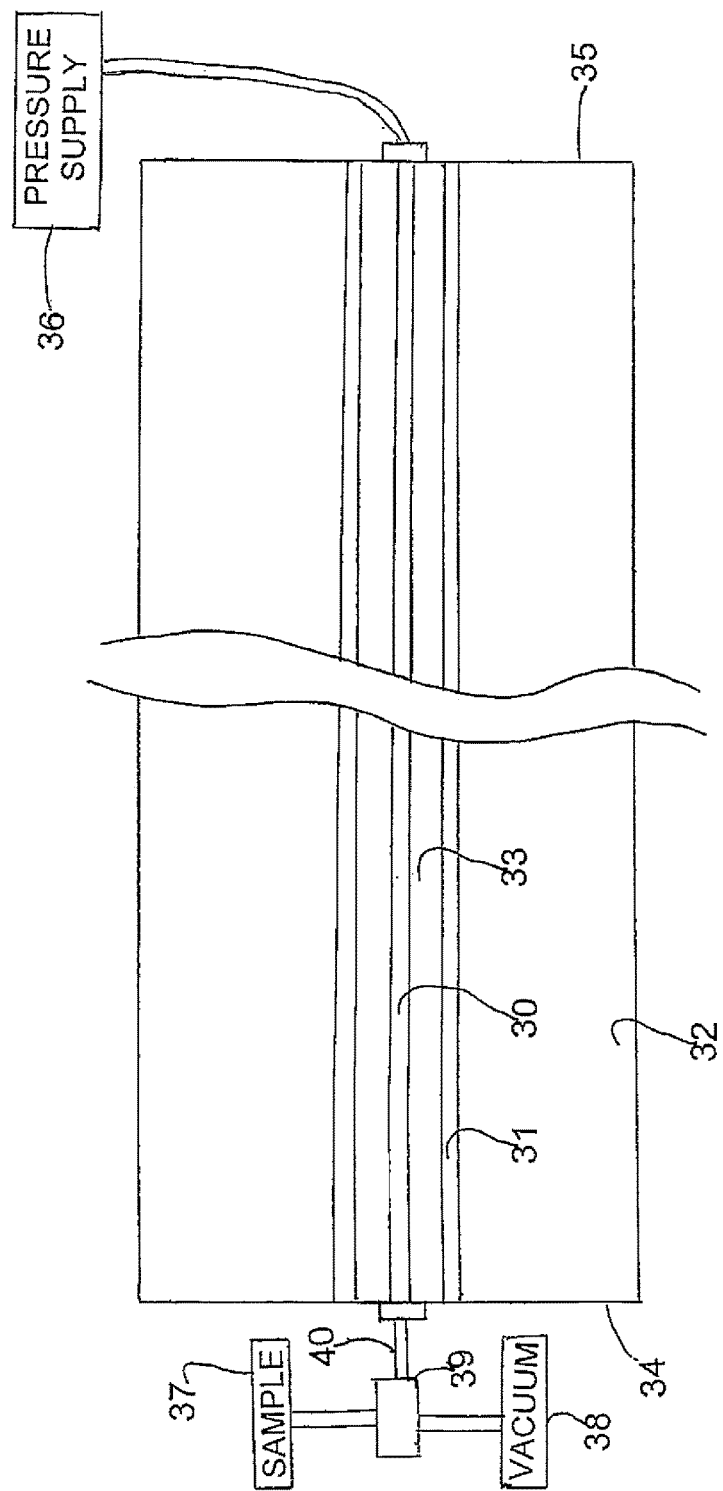
FIG. 2 is a vertical cross-sectional view longitudinally through a concrete member at a bonded post-tensioned reinforcing cable showing fluid injection into ends of the cable in a method according to the present invention.
Figure 3:
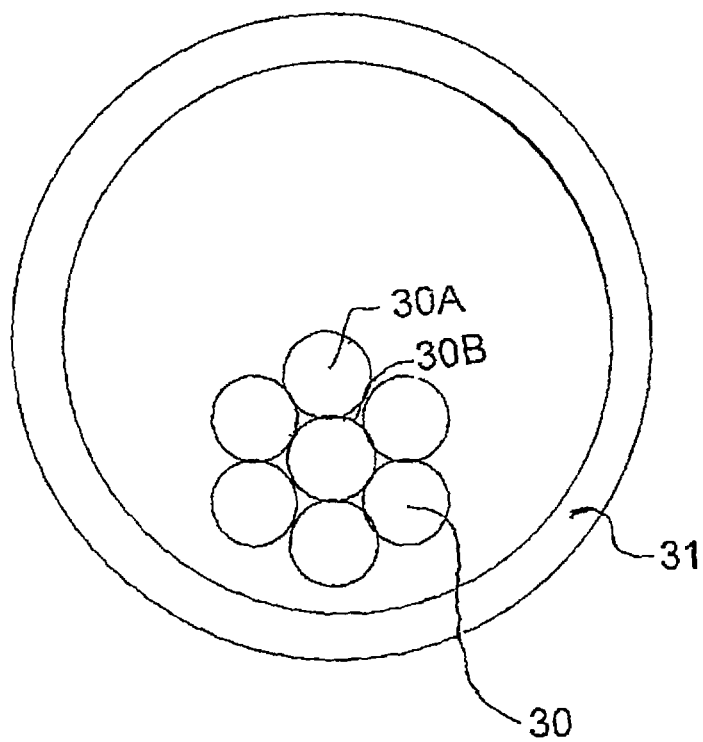
FIG. 3 is a cross-sectional view through the cable and surrounding sleeve of the concrete member of FIG. 2.

In FIGS. 2 and 3, the method is used with a post-tensioned system in which the cable 30 formed by wires 30A with interstices 30B is contained within a tubular container 31 extending along the concrete member 32 between the ends 34, 35. The wires of the cable are intimately surrounded by a filler material or grout 33 inserted into the tubular container 31 after tensioning of the cable 30 within the tubular container so that the filler material 33 is bonded intimately to the wires of the cable 30. In many cases multiple cables are present inside a singular tubular container (duct) wherein the filler material surrounds each of the cables. The duct assembly containing multiple cables is often referred to as a tendon or multi-strand assembly.

Again, the method comprising inserting a fluid into interstitial spaces 30B between the wires of the cable at a first location at the end 35 along the cable and causing the fluid to pass through the interstitial spaces between the wires of the cable to a second location at the end 34 along the cable.

In FIGS. 2 and 3, the fluid comprises a gas from a pressurized supply 36 arranged to effect a drying action on the wires of the cable to expel moisture from the interstitial spaces between the wires. In this case the gas may be used in a testing procedure to drive moisture from the interstitial spaces between the wires, which is then collected at the end 34 (or an alternate location) at a sample extractor 37 at an outlet 40 for analysis of a moisture content. In this way an initial testing procedure can be provided which detects the presence of any moisture and then goes onto a remediation process if moisture is detected.

A vacuum pump 38 can be provided connected to the outlet 40 to assist in drawing the gas more effectively along the path. A valve 39 controls the connection of the outlet 40 to the sample collector 37 or to the vacuum 38.

Similar to the previous example illustrated in FIG. 1, liquid can be injected into the interstices and can provide benefits similar to the example previously described.

Figure 4:
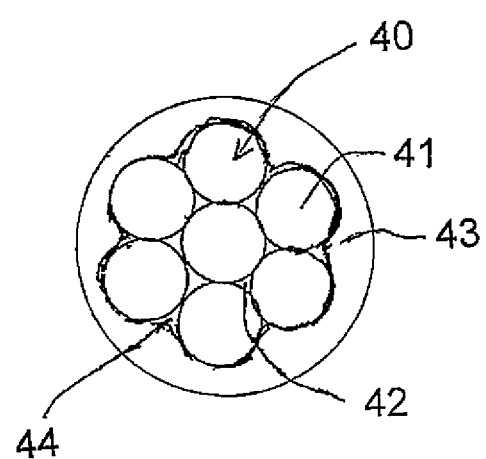
FIG. 4 is a cross-sectional view through an un-bonded post-tensioned cable with surrounding plastic sleeves showing the interstices of the cable containing the injected fluid.

In FIG. 4 the cable 40 comprises an array of wires 41 confined together to form an elongate cable with interstices 42 where the cable 40 is contained within an extruded plastic sleeve 43 extruded onto the cable. There is provided an un-bonded filler material, typically grease 44, between the cable 40 and the sleeve 43 arranged to allow sliding of the cable within the sleeve during tensioning.

The intimate engagement of the extruded jacket or sleeve 43 and the penetration of the inside surface of the sleeve into the exterior interstices of the wires around the cable causes the grease 44 to be contained or compressed onto the exterior surfaces around the wires 41 of the cable both around the outside of the wires and into the interstices between the wires so that there are no paths around the wires within the sleeve.

As explained and shown previously the fluid is injected into interstitial spaces 42 between the wires of the cable 41 at a first location along the cable and the fluid passes through the interstitial spaces between the wires of the cable to a second location along the cable.

The invention claimed is:

1. A method for use with a steel reinforcing cable embedded in a member comprising concrete;
    wherein the cable comprises an array of wires extending along the concrete for providing reinforcement thereto;
    wherein the wires are wound in a helix so as to hold them as a confined twisted array with each wire butting against its neighbors and held in contact with its neighbors by loads therebetween generated by tension on the confined twisted array;
    wherein the cable is intimately surrounded by a covering material which is engaged with a periphery of the cable so that there are insufficient interconnected spaces between the cable and the covering material to allow passage of fluid along the cable between the cable and the covering material;
    the method comprising:
        exposing at least part of at least some of the wires of the confined twisted array at a first location along the cable;
        inserting a fluid into interstitial spaces between the wires of the cable at the first location along the cable;
        wherein said at least part of at least some of the wires of the confined twisted array are exposed for said insertion at said first location either at a confined twisted end of the confined twisted array or at a side face of the confined twisted array;

where the insertion occurs directly into the interstitial spaces between the wires at said at least part of said at least some of the wires;

and causing the fluid to pass through the interstitial spaces between the wires of the cable to a second location along the cable.

2. The method according to claim 1 wherein the fluid is selected to reduce corrosion of the steel wires of the cable.

3. The method according to claim 1 wherein the fluid comprises corrosion inhibiting material.

4. The method according to claim 3 wherein the corrosion inhibiting material is selected from the group consisting of:
Amines;
Amino alcohol;
Amino carboxylate;
Calcium sulfonate;
Organofunctional silane, silane, siloxane or silicone;
Grease amine;
Oil amine;
Amine salts with nitrous of chromic acids;
Amine salts with carbonic acid, carbamic acid, acetic acid, substituted benzoic acids and organic esters of nitrous acid, phthalic acid or carbonic acid;
Primary, secondary and tertiary aliphatic amines;
Cycloaliphatic and aromatic amines;
Polymethylene amines;
Mixtures of nitrites, urea, hexamethylene tetramine and ethanolamines; and
Nitrobenzene and 1-Nitronaphthalene.

5. The method according to claim 4 wherein the corrosion inhibiting material comprises Calcium sulfonate or Organofunctional silane.

6. The method according to claim 1 wherein the fluid comprises a liquid arranged to expel moisture from the interstitial spaces between the wires of the cable.

7. The method according to claim 1 wherein the fluid impregnates a region of the covering material surrounding the cable.

8. The method according to claim 7 wherein the fluid interacts with the covering material to change its properties within the impregnated region.

9. The method according to claim 7 wherein the fluid interacts with the covering material to reduce permeability of the impregnated region.

10. The method according to claim 7 wherein the fluid interacts with the covering material to increase the electrical resistivity of the impregnated region.

11. The method according to claim 1 wherein the fluid forms a protective film on exposed portions of the wires.

12. The method according to claim 1 wherein the fluid comprises a liquid arranged to spread outwardly from the cable into the surrounding covering material so as to generate a hydrophobic zone around the cable.

13. The method according to claim 1 wherein the fluid comprises a liquid which is arranged to increase in viscosity after inserting into the cable.

14. The method according to claim 1 wherein the fluid is a liquid which is arranged to set-up after inserting into the cable.

15. The method according to claim 1 wherein the fluid comprises a liquid selected from the group consisting of:
Silane,
Siloxane, silicone,
Oil,
Organic solvent,
Calcium sulfonate, and
Polymer resin.

16. The method according to claim 1 wherein the fluid comprises a liquid selected from the group consisting of:
Water,
Water containing dissolved salts, and
Water containing suspended particles.

17. The method according to claim 1 wherein the fluid comprises a gas arranged to effect a drying action on the wires of the cable to expel moisture from the interstitial spaces between the wires.

18. Method according to claim 17 wherein the application of the gas is continued to effect drying of the covering material adjacent to the cable.

19. The method according to claim 1 wherein the fluid comprises a gas arranged to drive moisture from the interstitial spaces between the wires and wherein the gas and the moisture are collected at the second location for analysis of a moisture content thereof.

20. The method according to claim 1 wherein the covering material is concrete where the cable is directly surrounded by the concrete of the concrete member.

21. The method according to claim 1 wherein the covering material is a grout within a tubular containment member.

22. The method according to claim 21 wherein more than one cable is present within the tubular containment member.

23. The method according to claim 1 wherein the covering material comprises a jacket extruded onto the periphery of the cable which contains an un-bonded filler material to allow the cable to slide inside the jacket during tensioning.

24. The method according to claim 1 wherein the covering material intimately surrounding the cable is the concrete or is a filler material within a tubular container.

25. The method according to claim 24 wherein the fluid is different from the concrete and different from the filler material.

26. The method according to claim 1 wherein said at least part of at least some of the wires of the confined twisted array are exposed at a side face of the array spaced from an end of the array of the confined twisted array and the insertion occurs at the side face.

27. A method for use with a steel reinforcing cable embedded in a surrounding covering material comprising concrete or mortar or grout;
wherein the cable is intimately enclosed in and exterior wires of the cable are engaged by the surrounding covering material;
wherein the cable comprises an array of wires confined together to form an elongate cable extending along the concrete for providing reinforcement thereto;
the method comprising:
exposing the wires of the cable at a first location along the cable;
introducing a liquid into interstitial spaces between the exposed wires within the cable at the first location along the cable;
wherein the liquid is different from the surrounding covering material;
where the insertion occurs directly into the interstitial spaces between the exposed wires;
causing the liquid to pass along the cable to a second location along the cable;
and causing the liquid arranged to spread outwardly from the cable to impregnate into the surrounding covering material so as to generate an impregnated zone around the cable.

28. The method according to claim 27 wherein the impregnated zone around the cable is hydrophobic.

29. The method according to claim 27 wherein the impregnated zone around the cable includes a corrosion inhibiting material.

30. The method according to claim 27 wherein the impregnated zone around the cable has an increased electrical resistance.

31. The method according to claim 27 wherein the impregnated zone around the cable has a reduced permeability.

32. The method according to claim 27 wherein the fluid comprises a liquid which is arranged to increase in viscosity after inserting into the cable.

33. The method according to claim 27 wherein the fluid is a liquid which is arranged to set-up after inserting into the cable.

34. The method according to claim 27 wherein the fluid comprises a liquid selected from the group consisting of:
Silane, siloxane, silicone,
Organofunctional silane,
Oil,
Mineral oil,
Calcium sulfonate, and
Polymer resin.

35. A method for use with a steel reinforcing cable embedded in a member comprising concrete;
wherein the cable comprises an array of wires extending along the concrete for providing reinforcement thereto;
wherein the cable is intimately surrounded by a covering material which is engaged with a periphery of the cable so that there are insufficient interconnected spaces between the cable and the covering material to allow passage of fluid along the cable between the cable and the covering material;
the method comprising:
 exposing at least part of at least some of the wires of the cable at a first location along the cable where the wires are exposed at a side face of the array spaced from an end of the array;
 inserting a fluid into interstitial spaces between the wires of the cable at said first location at the side face of the array;
 where the insertion occurs directly into the interstitial spaces between the wires at said side face of the array;
 and causing the fluid to pass through the interstitial spaces between the wires of the cable to a second location along the cable.

36. The method according to claim 35 wherein the covering material intimately surrounding the cable is the concrete or is a filler material within a tubular container.

* * * * *